US011918236B2

(12) United States Patent
Patel et al.

(10) Patent No.: US 11,918,236 B2
(45) Date of Patent: *Mar. 5, 2024

(54) DRILL ALIGNMENT GUIDE

(71) Applicant: WRIGHT MEDICAL TECHNOLOGY, INC., Memphis, TN (US)

(72) Inventors: Vinay D. Patel, Memphis, TN (US); Shannon D. Cummings, Hernando, MS (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,481

(22) Filed: Jan. 19, 2023

(65) Prior Publication Data
US 2023/0157712 A1 May 25, 2023

Related U.S. Application Data

(60) Continuation of application No. 17/243,869, filed on Apr. 29, 2021, now Pat. No. 11,583,295, which is a division of application No. 16/136,843, filed on Sep. 20, 2018, now Pat. No. 11,020,130.

(51) Int. Cl.
*A61B 17/17* (2006.01)
*A61B 17/80* (2006.01)

(52) U.S. Cl.
CPC ...... *A61B 17/1717* (2013.01); *A61B 17/1728* (2013.01); *A61B 17/808* (2013.01)

(58) Field of Classification Search
CPC ............ A61B 17/1717; A61B 17/1725; A61B 17/1728; A61B 17/1775
See application file for complete search history.

(56) References Cited

U.S. PATENT DOCUMENTS

| | | |
|---|---|---|
| 2013/0085502 A1 | 4/2013 | Harrold |
| 2016/0367270 A1 | 12/2016 | Garlock et al. |
| 2018/0110542 A1* | 4/2018 | DeVasConCellos ... A61B 17/86 |
| 2018/0242988 A1 | 8/2018 | Dacosta et al. |
| 2019/0117238 A1* | 4/2019 | Levitt .................... A61B 17/60 |
| 2019/0142488 A1 | 5/2019 | Wang et al. |
| 2020/0222065 A1 | 7/2020 | Ingman et al. |

* cited by examiner

*Primary Examiner* — Si Ming Ku
(74) *Attorney, Agent, or Firm* — DUANE MORRIS LLP

(57) ABSTRACT

A surgical drill alignment guide is disclosed that can provide an accurate trajectory for placement of a bone screw along a longitudinal axis of a bone.

17 Claims, 13 Drawing Sheets

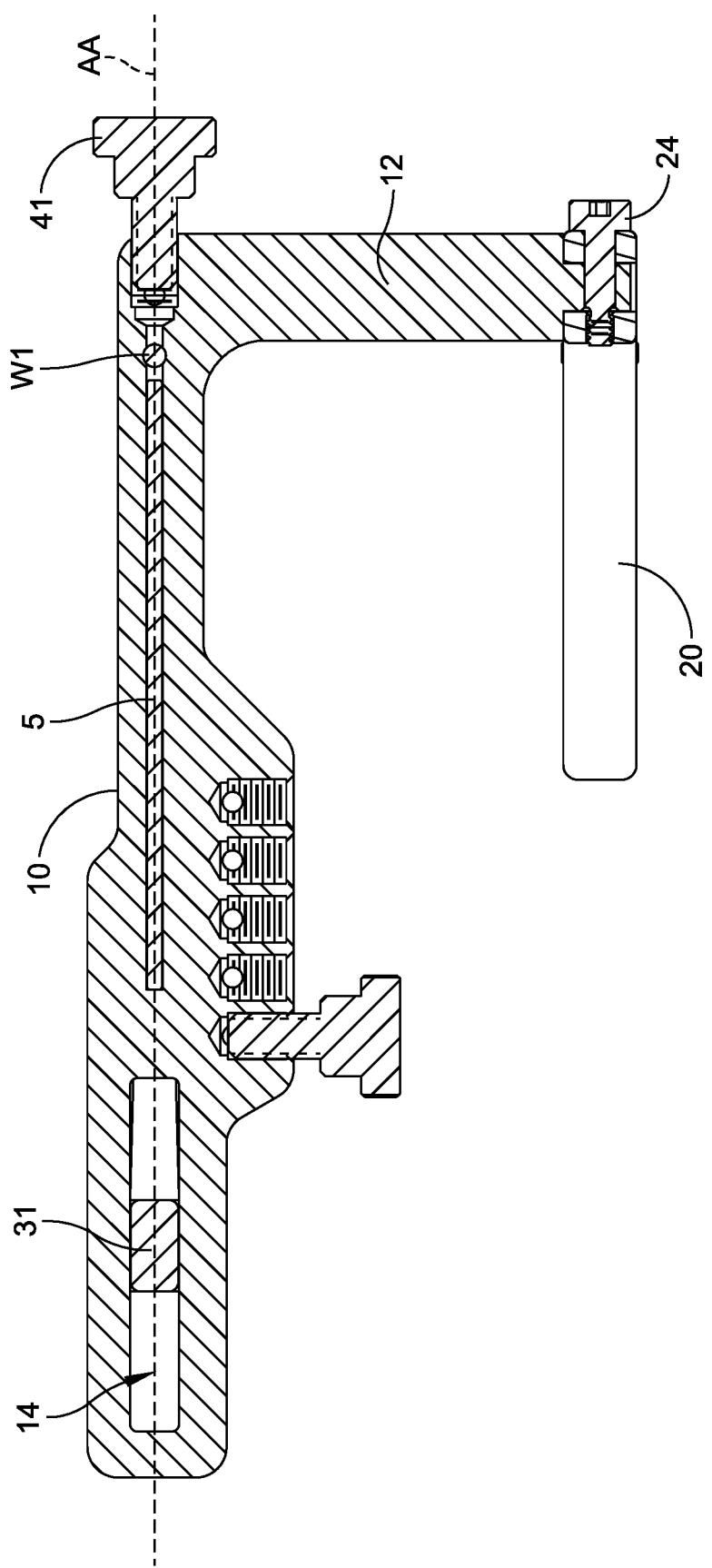
FIG. 3A SECTION D-D

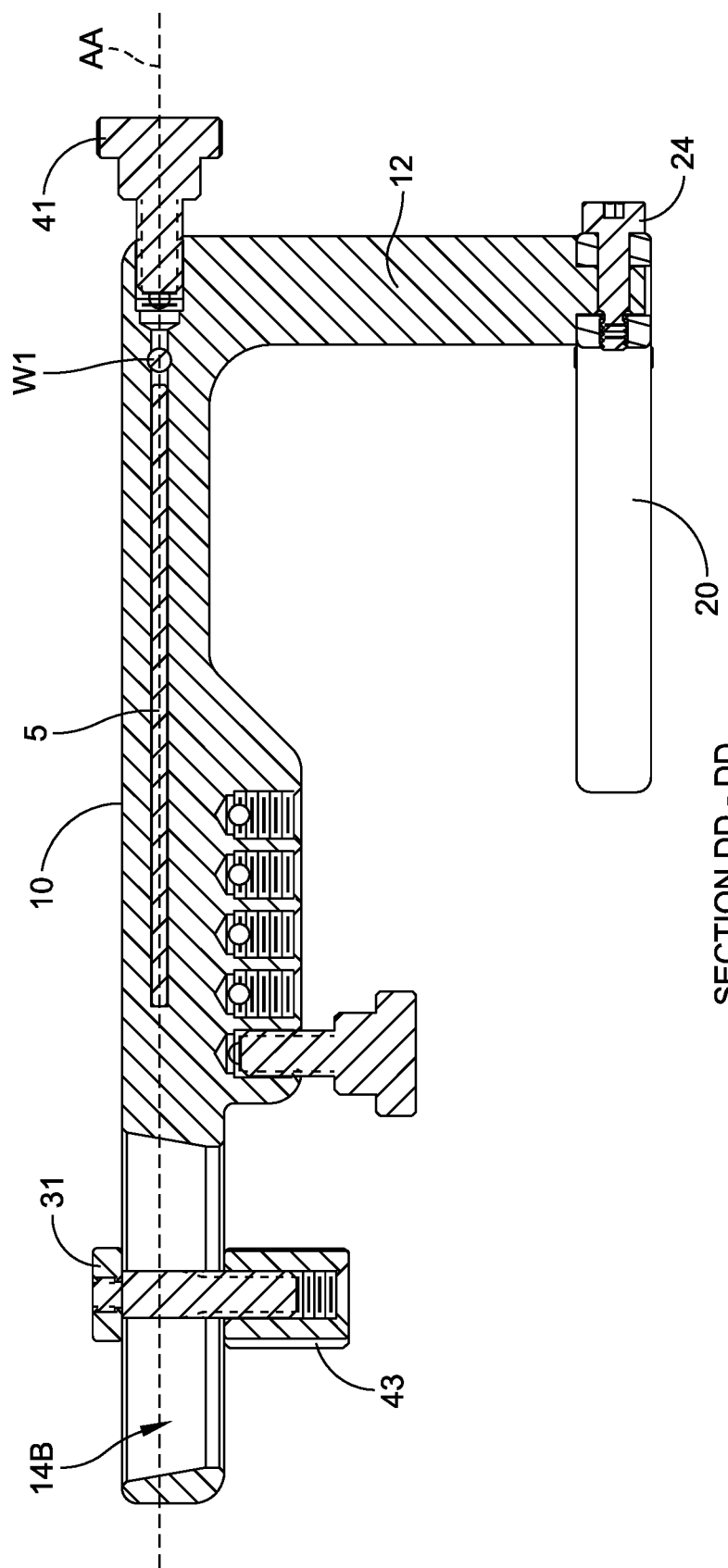
FIG. 3B  SECTION DD - DD

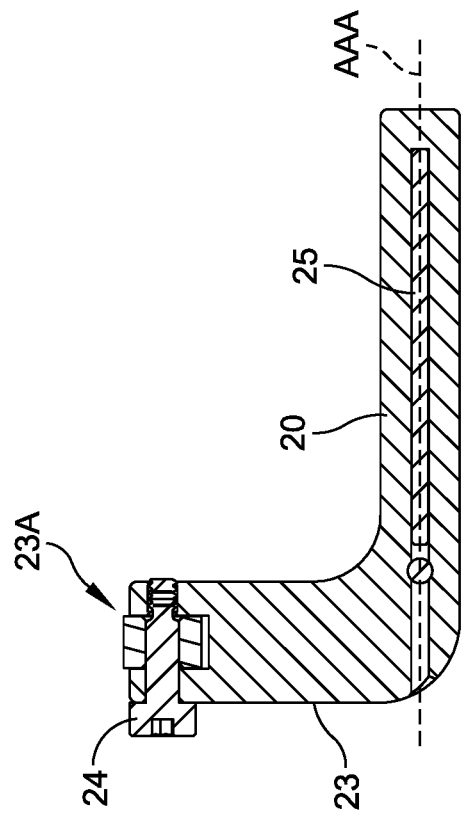
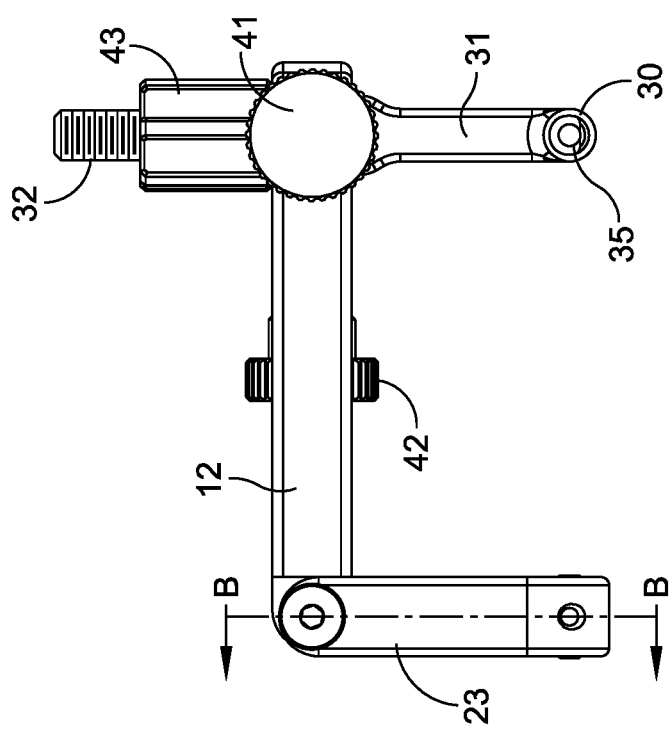
FIG. 5A
FIG. 4A

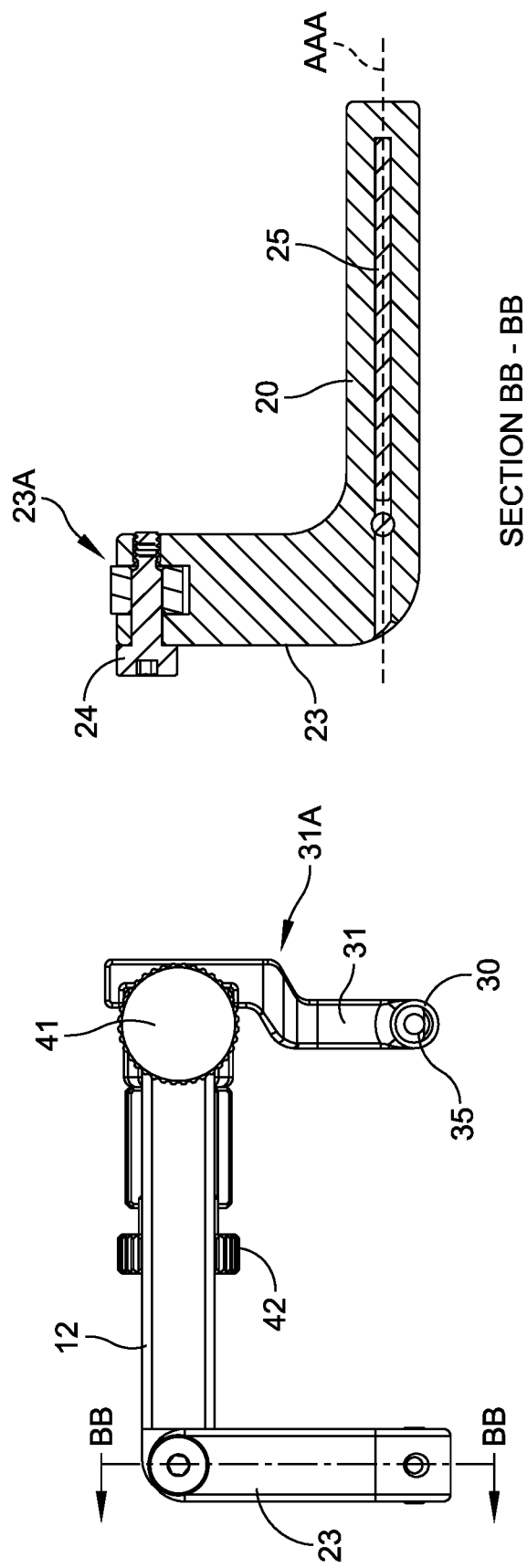

DRILL ALIGNMENT GUIDE

CROSS-REFERENCE TO RELATED APPLICATIONS

This application is a continuation of U.S. patent application Ser. No. 17/243,869, filed Apr. 29, 2021, which is a divisional application of U.S. patent application Ser. No. 16/136,843, filed Sep. 20, 2018 (now U.S. Pat. No. 11,020, 130), the entire contents of which is incorporated herein by reference.

FIELD OF DISCLOSURE

The present disclosure relates to a targeting guide that can be used to provide an accurate trajectory for placement of a bone screw along a longitudinal axis of a bone.

BACKGROUND

A successful treatment of bone fractures often depend on accurate placement of k-wires or bone screws for reducing or compressing the fracture. Often, a surgeon must visually estimate the trajectory of a drill bit for drilling a hole along a long axis of a bone to prepare for a k-wire or a bone screw. When these bones are inside the patient's body such as a hand or a foot, visually estimating the trajectory is difficult. Thus, a drill alignment or a targeting guide that can facilitate such procedure is desired.

SUMMARY

Disclosed herein is a surgical drill alignment guide that can be used to provide an accurate trajectory for placement of a bone screw along the long axis of a bone. One example of such application is for providing an accurate trajectory for placement of a bone screw along a fifth metatarsal bone for treating a Jones fracture.

In some embodiments, the surgical drill alignment guide assembly comprises a first alignment arm having a first end, a second end, and a longitudinal axis extending from the first end to the second end, the first end of the first alignment arm having a first through hole for receiving a first wire, and at least one second through hole provided between the first end and the second end for receiving a second wire.

The first through hole extends through the first end of the first alignment arm in an orthogonal orientation to and intersecting the longitudinal axis of the first alignment arm. The at least one second through hole extends through the first alignment arm in an orthogonal orientation to the longitudinal axis of the first alignment arm.

A second alignment arm has a first end, a second end, and a longitudinal axis extending between the first end and the second end. The first end of the second alignment arm is attached to the first end of the first alignment arm, wherein the second alignment arm is oriented so that its longitudinal axis is in parallel relation to the longitudinal axis of the first alignment arm. A drill guide is attached to the first alignment arm between the second end and the at least one second through hole. The drill guide comprises an arm having a hollow shaft that extends therethrough for receiving and guiding a drill bit or a k-wire. The hollow shaft extends in parallel relation to the longitudinal axis of the first alignment arm and the longitudinal axis of the second alignment arm. The hollow shaft is in-plane with the first alignment arm's longitudinal axis in a first plane, and in-plane with the second alignment arm's longitudinal axis in a second plane, wherein the first plane and the second plane are orthogonal to each other.

A method of using the drill alignment guide assembly is also disclosed.

BRIEF DESCRIPTION OF THE DRAWINGS

The inventive surgical drill alignment guide assembly of the present disclosure will be described in more detail in conjunction with the following drawing figures. The structures in the drawing figures are illustrated schematically and are not intended to show actual dimensions.

FIG. 3A is a sectional view of the surgical drill alignment guide assembly of FIGS. 1A and 2A, taken through the sectional line D-D marked in FIG. 2A.

FIG. 3B is a sectional view of the surgical drill alignment guide assembly of FIGS. 1B and 2B, taken through the sectional line DD-DD marked in FIG. 2B.

FIG. 4A is a side view of the surgical drill alignment guide assembly of FIGS. 1A and 2A.

FIG. 4B is a side view of the surgical drill alignment guide assembly of FIGS. 1B and 2B.

FIG. 5A is a sectional view of the surgical drill alignment guide assembly taken through the sectional line B-B marked in FIG. 4A.

FIG. 5B is a sectional view of the surgical drill alignment guide assembly taken through the sectional line BB-BB marked in FIG. 4B.

DETAILED DESCRIPTION

Figure 1A:
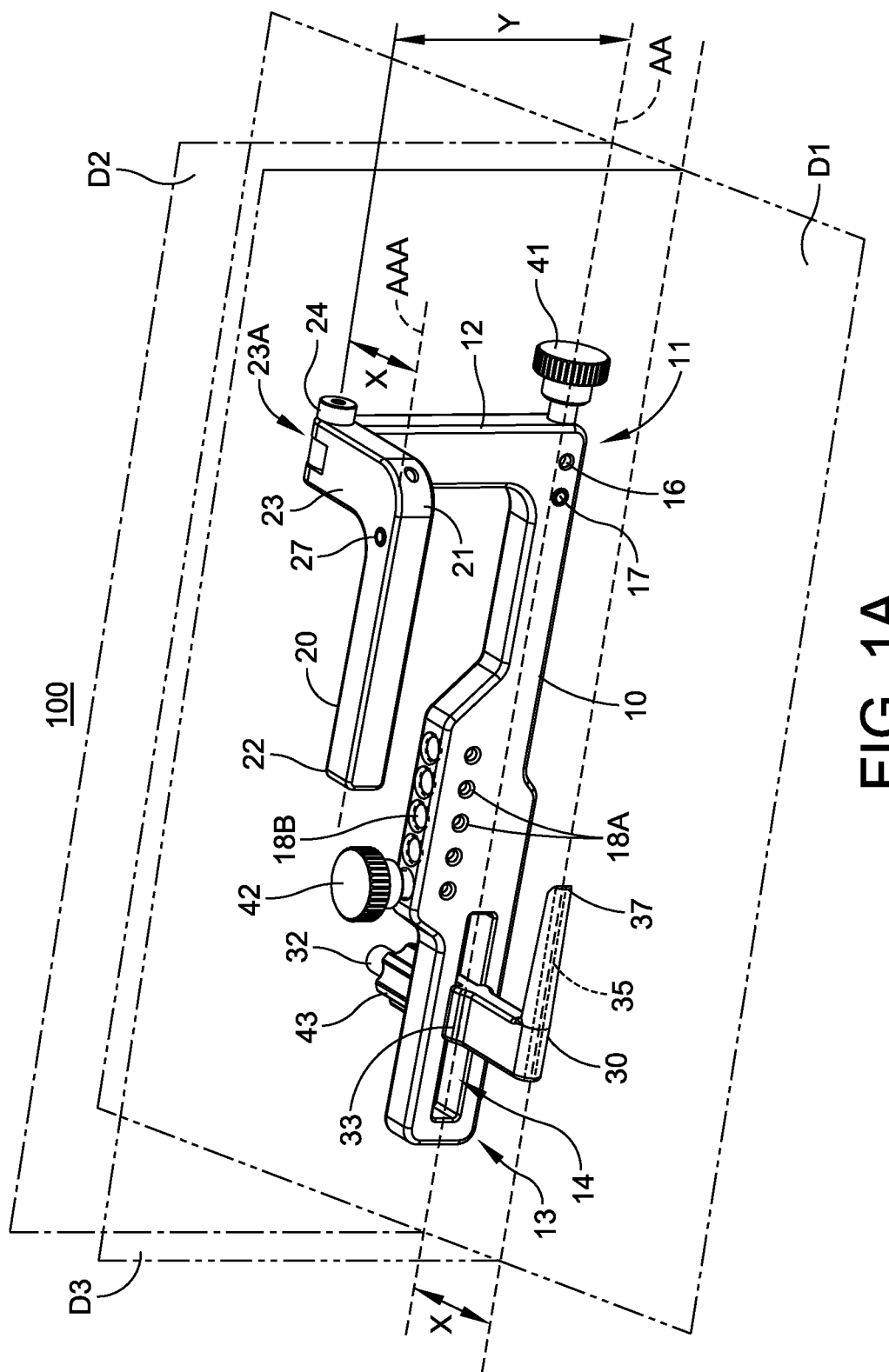
FIG. 1A is an isometric view of a surgical drill alignment guide assembly according to an embodiment of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIG. 1A, a surgical drill alignment guide assembly 100 for aligning a drill guide 30 along a longitudinal axis A of a fifth metatarsal bone is disclosed. The drill alignment guide assembly 100 comprises a first alignment arm 10, a second alignment arm 20, and a drill guide 30.

The first alignment arm 10 has a first end 11, a second end 13, and a longitudinal axis AA extending from the first end 11 to the second end 13. The second alignment arm 20 has a first end 21, a second end 22, and a longitudinal axis AAA extending from the first end 21 to the second end 22.

The second alignment arm 20 is attached to the first alignment arm near or at the first end 11 of the first alignment arm 10. The second alignment arm 20 is oriented so that its longitudinal axis AAA is in parallel relation to the longitudinal axis AA of the first alignment arm 10. Because of this arrangement, when the longitudinal axis AA of the first alignment arm is aligned parallel to the longitudinal axis A of the fifth metatarsal bone B1, the second alignment arm's longitudinal axis AAA is also aligned parallel to the longitudinal axis A of the fifth metatarsal bone B1.

The first end 11 of the first alignment arm 10 is configured to attach to a first wire W1 that is placed into a distal portion of the fifth metatarsal bone perpendicular to the longitudinal axis A of the fifth metatarsal bone. In some embodiments, the first alignment arm 10 is configured so that the attachment between the first alignment arm 10 and the first wire W1 can be releasably locked so that the position of the first alignment arm 10 along the length of the first wire W1 can be fixed then unlocked when the drill alignment procedure is completed.

As shown in FIG. 1A, the first end 11 of the first alignment arm 10 is provided with a through hole 16 that extends through the full thickness of the first alignment arm 10 for receiving the first wire W1. Preferably, the through hole 16 extends through the first alignment arm 10 straight and oriented orthogonal to the longitudinal axis AA of the first alignment arm 10. In use, the first wire W1 would be inserted into the distal end of the fifth metatarsal bone from the lateral side of the patient's foot such that the first wire W1 is substantially perpendicular to the long axis A of the fifth metatarsal bone. The through hole 16 extends through the first alignment arm 10 straight and oriented orthogonal to the longitudinal axis AA of the first alignment arm 10. This ensures that when the alignment guide 100 is attached to the first wire W1 by fitting the through hole 16 over the first wire W1, the first wire W1 and the longitudinal axis AA of the first alignment arm 10 are orthogonal to each other.

The first alignment arm 10 is configured and adapted to be able to lock the first wire W1 in place in the through hole 16. There are many known locking mechanisms that can be employed here such as a CAM locking mechanism or a set screw arrangement. In the example illustrated in FIGS. 1A, 3A, and 6, the through hole 16 is provided with a setscrew 41 for locking the first wire W1 extending through the through hole 16. As shown in the cross-sectional view in FIG. 3A, the setscrew 41 threads into the first end 11 of the first alignment arm 10 orthogonal to the through hole 16. Thus, the first wire W1 extending through the through hole 16 can be locked in position by tightening the setscrew 41 against the first wire W1.

The first alignment arm 10 is also provided with at least one second through hole 18A for receiving a second wire W2 that gets placed into a mid-foot bone B2 that is associated with the fifth metatarsal bone B1. Like the first through hole 16, the second through hole 18A also extends through the thickness of the first alignment arm 10 oriented perpendicular to the longitudinal axis AA of the first alignment arm 10. This ensures that a second wire W2 inserted through the second through hole 18A is parallel to the first wire W1 and, in turn, also orthogonal to the long axis A of the fifth metatarsal bone B1. In some embodiments, the first alignment arm 10 is configured to lock the position of the second wire W2 placed through the second through hole 18A. The second wire W2 is for a fixing the orientation of the drill alignment guide assembly 100 to the patient's mid-foot bone B2, so the second through hole 18A is located at an appropriate distance from the first through hole 16 so that the position of the second through hole 18A reaches the patient's mid-foot bone B2.

Figure 1B:
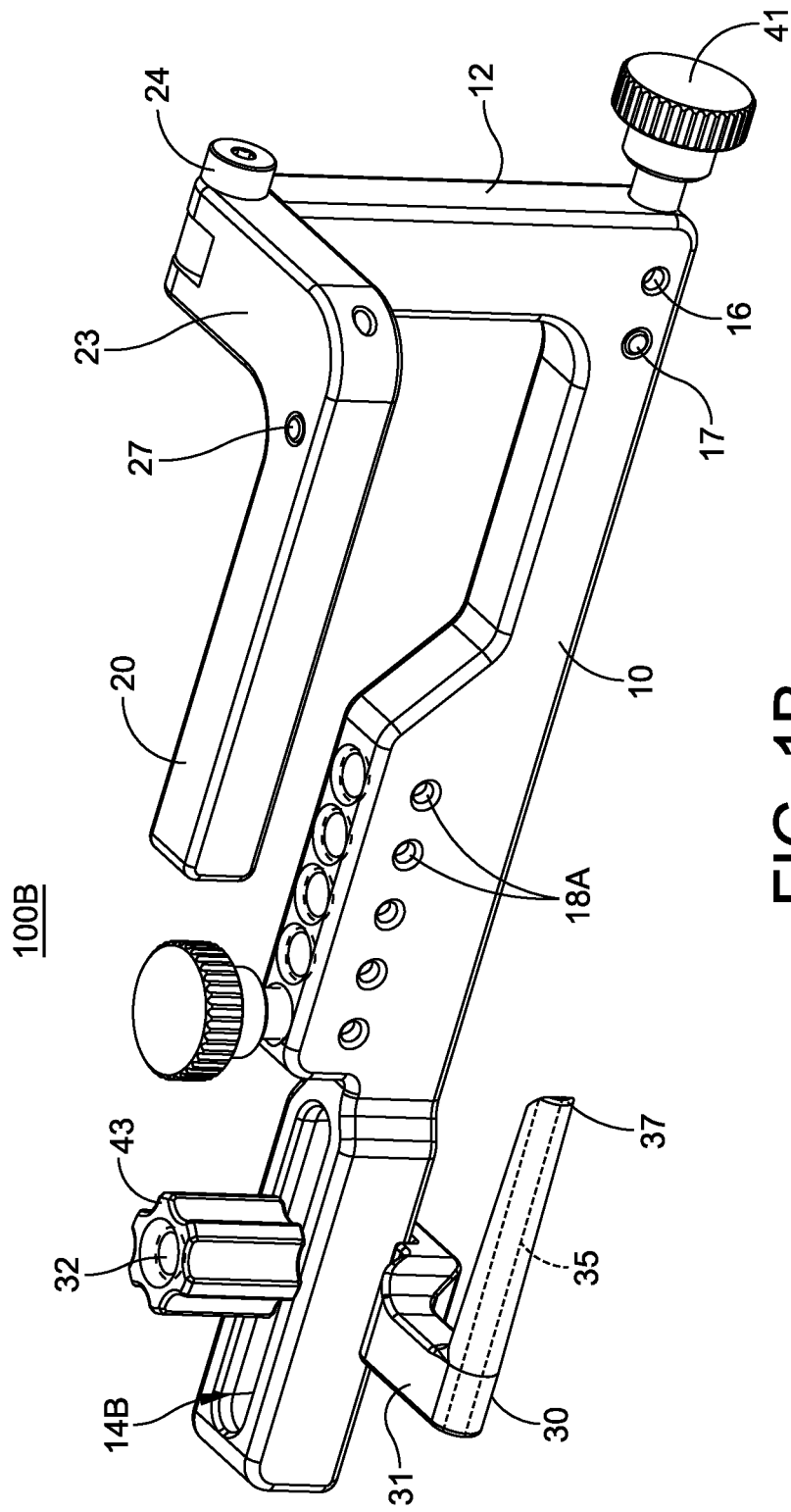
FIG. 1B is an isometric view of a surgical drill alignment guide assembly according to another embodiment of the present disclosure.
Figure 2A:
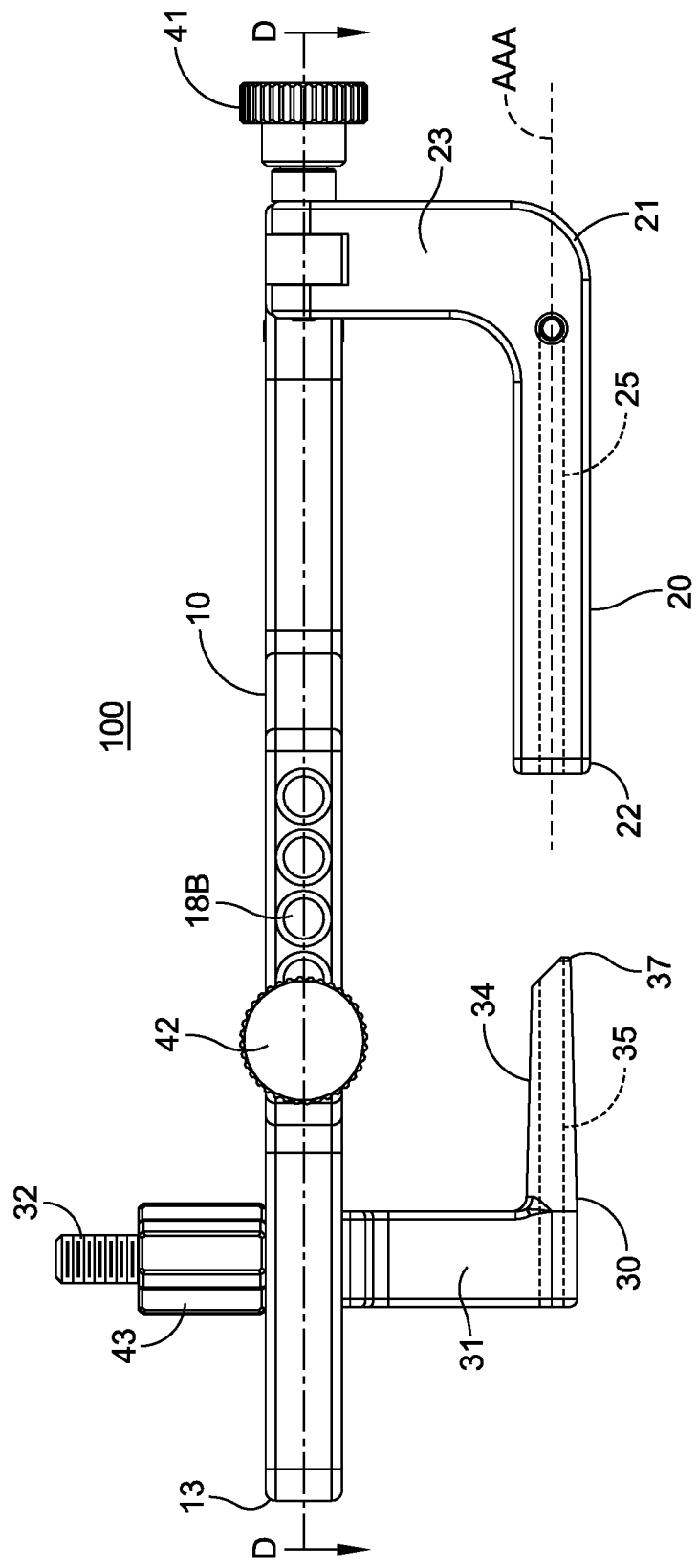
FIG. 2A is a top-down view of the surgical drill alignment guide assembly of FIG. 1A.
Figure 2B:
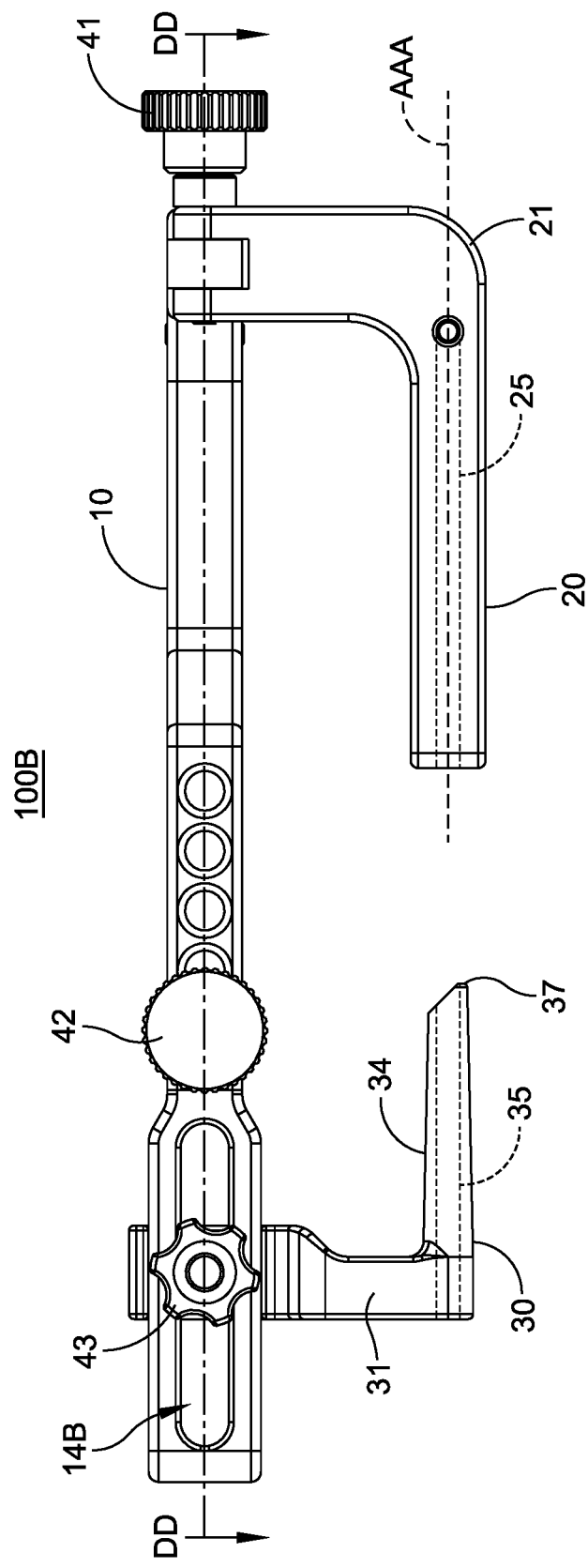
FIG. 2B is a top-down view of the surgical drill alignment guide assembly of FIG. 1B.

In some embodiments, a plurality of second through holes 18A are provided as shown in FIGS. 1A and 1B in order to provide a more robust functionality to the drill alignment guide 100 in terms of its ability to accommodate a wide range of patient's foot sizes. The plurality of second through holes 18A are provided side by side along a portion of the first alignment arm 10 as shown so that a variety of choices are available for the distance between the first through hole 16 and the second through hole 18A to accommodate fifth metatarsal bones of different lengths.

The surgical drill alignment guide 100 can be configured to lock the second wire W2 extending through the second through hole 18A. There are many known locking mechanisms that can be employed here such as a CAM locking mechanism or a set screw arrangement. In the example illustrated here, the first alignment arm 10 is provided with a second set screw 42 for locking the second wire W2 extending through a through hole 18A. As shown in the cross-sectional view in FIG. 3A, the setscrew 42 threads into the first alignment arm 10 orthogonal to the through hole 18A. Thus, the second wire W2 extending through the through hole 18A can be locked in position by tightening the setscrew 42 against the second wire W2. Where there are more than one second through hole 18A, each of the second though hole 18A will be provided with a second set screw 42.

Referring to FIGS. 3A, 3B, the first alignment arm 10 also has a radio-opaque alignment wire 5 provided along the longitudinal axis AA of the first alignment arm so that the alignment wire 5 can be used to check the alignment of the first alignment arm 10 under a fluoroscope.

The second alignment arm 20 has a first end 21 and a second end 22, and a longitudinal axis AAA extending between the first end and the second end. The second alignment arm 20 is disposed in parallel relation to and attached to the first alignment arm 10, whereby the longitudinal axis AAA is in parallel relation to the longitudinal axis AA of the first alignment arm 10. Thus, when the longitudinal axis AA of the first alignment arm 10 is positioned in an alignment parallel to the longitudinal axis A of the fifth metatarsal bone B1, the longitudinal axis AAA of the second alignment arm 20 is also in parallel relationship to the longitudinal axis A of the fifth metatarsal bone B1.

In some embodiments, the second alignment arm 20 is attached to the first alignment arm 10 by a hinge joint 23A. In the example shown in FIGS. 1A and 1B, the first alignment arm 10 has a vertical connecting arm 12 and the second alignment arm 20 is connected to the extension section 12 by the hinge joint 23A. The hinge joint 23A is configured to allow the second alignment arm 20 to turn 180° about the hinge joint from the position shown in FIGS. 1A and 1B to the position shown in FIG. 6. This allows the surgical drill alignment guide assembly 100 to be used on either the left foot or the right foot. For example, in FIG. 6, the surgical drill alignment guide assembly 100 is installed on the patient's right foot aligning the drill guide 30 with the fifth metatarsal bone B1 on the right foot. In this configuration, one can see that the second alignment arm 20 has been flipped over 180° about the hinge 23A from the configuration shown in FIG. 1A. The drill guide 30 is also connected to the first alignment arm 10 from the opposite side than the configuration shown in FIG. 1A.

Figure 6:
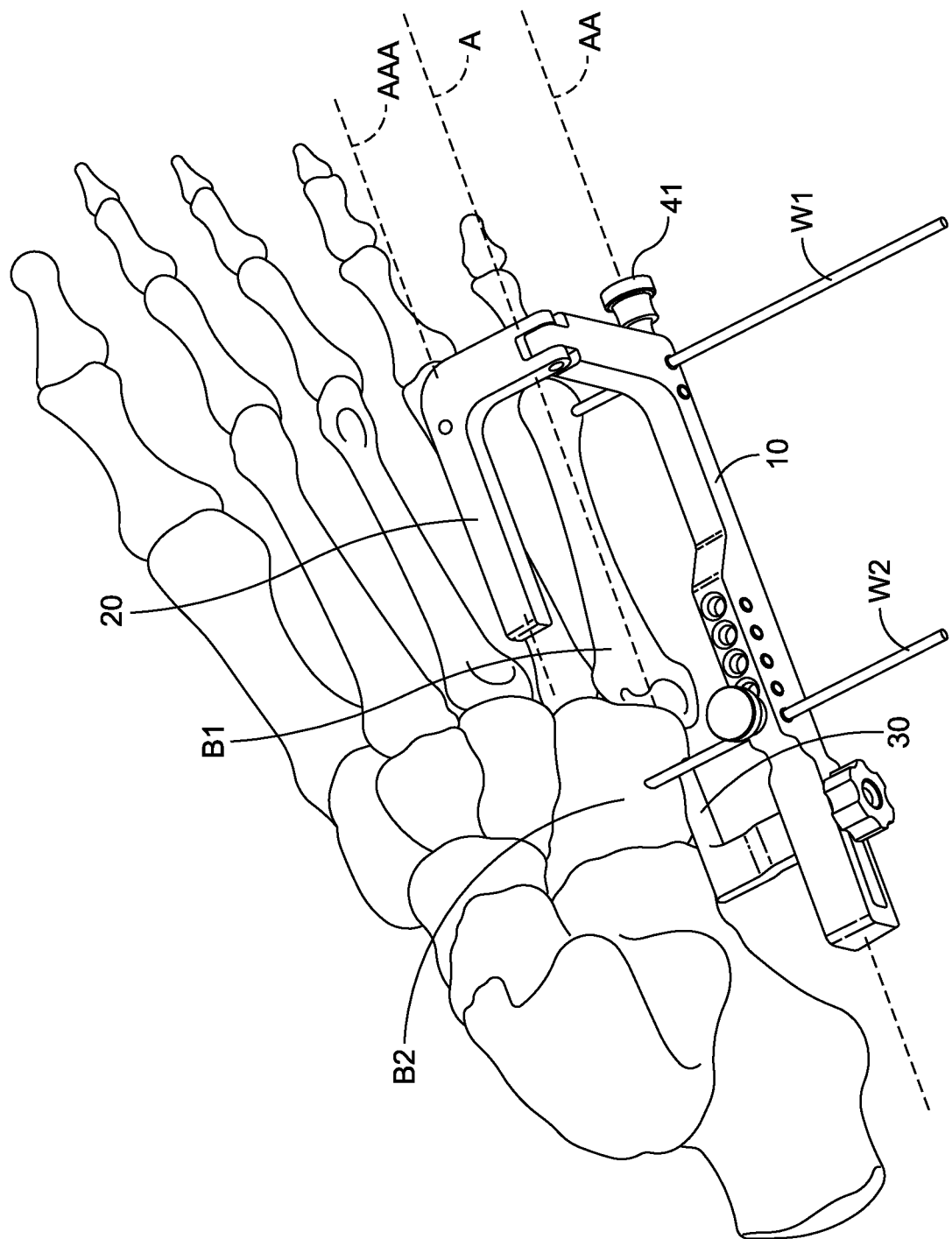
FIG. 6 is a perspective view of the surgical drill alignment guide assembly of FIG. 1A in its installed position with respect to a human right foot showing the alignment guide assembly's arrangement with the fifth metatarsal bone.
Figure 7:
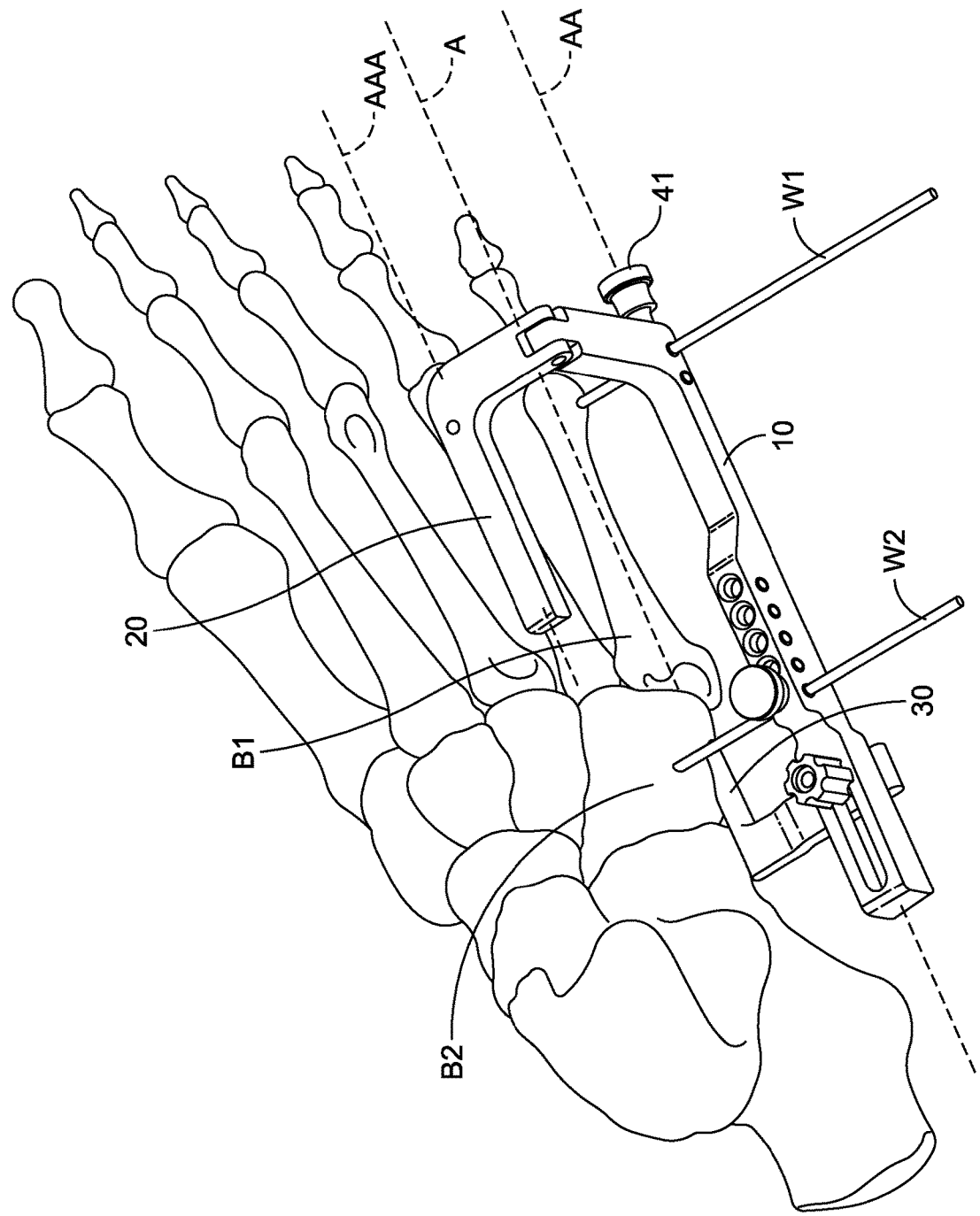
FIG. 7 is a perspective view of the surgical drill alignment guide assembly of FIG. 1B in its installed position with respect to a human right foot showing the alignment guide assembly's arrangement with the fifth metatarsal bone.

The same ability to be used either on the left foot or the right foot is applicable to the embodiments of the drill alignment guide assembly shown in FIG. 1B and FIG. 7. In FIG. 1B and FIG. 7, the drill guide 30 and the second end 13 of the first alignment arm 10 are configured so that the drill guide 30 attaches to the first alignment arm 10 by fitting its stem 32 through the slot 14B in a vertical direction rather than the sideways engagement in the embodiments of FIG. 1A and FIG. 6.

The vertical connecting arm 12 positions the second alignment arm 20 a distance Y above the longitudinal axis AA of the first alignment arm 10. The distance Y is a distance that is sufficiently large to allow the second alignment arm 20 to be positioned above the patient's fifth metatarsal bone without contacting or interfering with the patient's foot.

In the embodiments illustrated in FIGS. 1A and 1B, the vertical connecting arm 12 extends from the first end 11 of the first alignment arm 10. However, the vertical connecting arm 12 can be connected to the first alignment arm 10 anywhere on the first alignment arm 10 as long as the second alignment arm 20 can be positioned above the fifth metatarsal bone B1 somewhere along the length of the fifth metatarsal bone B1 on the dorsal side of the patient's foot or below the fifth metatarsal bone B1 somewhere along the length of the fifth metatarsal bone B1 on the anterior side of the patient's foot. Whether the alignment procedure is carried out from the dorsal side or the plantar side of the patient's foot is at the discretion and preference of the surgeon but the drill alignment guide assembly 100 of the present disclosure is configured to be used in either direction.

The second alignment arm 20 is connected to the vertical connecting arm 12 by a connecting portion 23. The connecting portion 23 extends away from the vertical connecting arm 12 so that the longitudinal axis AAA of the second alignment arm 20 is at a distance X from the vertical plane D1 defined through the center of the vertical connecting arm 12 and the longitudinal axis AA of the first alignment arm 10. The center of the vertical connecting arm 12 here refers to the middle of the thickness of the vertical connecting arm 12.

Referring to FIGS. 1A, 1B, 2A, and 2B, the drill guide 30 is attached to the first alignment arm 10 between the second end 13 and the at least one second through holes 18A. The drill guide 30 comprises an arm 34 having a hollow shaft 35 for receiving and guiding a drill bit or a k-wire. The hollow shaft 35 extends through the length of the drill guide arm 34 in parallel relation to the longitudinal axis AA of the first alignment arm 10 and the longitudinal axis AAA of the second alignment arm 20.

In some embodiments, the drill guide 30 is slidably attached to the first alignment arm 10 so that the drill guide 30 can be moved along the longitudinal axis AA of the first alignment arm 10 and locate it at a desired position along the first alignment arm 10. The connection between the drill guide 30 and the first alignment arm is configured to be able to lock the drill guide 30 at a desired position.

The drill guide 30 can be attached to the first alignment arm 10 in any suitable configuration. The example in FIGS. 1A, 2A, 3A, 4A, 5A, and 6 show an embodiment where the drill guide 30 is attached to the first alignment arm 10 in a slidable manner through a slot 14 that is accessible from the side of the first alignment arm 10. The drill guide 30 has a stem portion 31 (labeled in FIG. 2A) that extends through the slot 14 and has a male threaded portion 32 onto which a female threaded nut 43 engages to lock the drill guide 30 in place. The stem portion 31 is configured to position the hollow shaft 35 of the drill guide 30 at the distance X from the longitudinal axis AA of the first alignment arm 10.

In this example, the stem portion 31 is provided with bump stoppers 33 to maintain the fixed distance X. (See FIG. 1A). Here, the distance X between the hollow shaft 35 and the longitudinal axis AA, we are referring to the distance between the central axis of the hollow shaft 35 (having a cylindrical shape) and the longitudinal axis AA. This ensures that the second alignment arm 20 can be used to align the drill guide 30 to the long axis A of the fifth metatarsal bone B1. The attachment between the drill guide 30 and the first alignment arm 10 is configured so that the hollow shaft 35 of the drill guide 30 is in parallel relation with the longitudinal axis AA of the first alignment arm 10 and also in the plane P1 defined by the longitudinal axis AA and the first wire W1 extending through the through hole 16. (See FIG. 8).

FIGS. 1B, 2B, 3B, 4B, 5B, and 7 show an embodiment where the drill guide 30 is attached to the first alignment arm 10 in a slidable manner through a slot 14B that is accessible from the top side of the first alignment arm 10. In this embodiment, the drill guide 30 has a stem portion 31 (labeled in FIG. 2B) that extends under the slot 14B and has a male threaded portion 32 that extends through the slot 14B onto which a female threaded nut 43 engages to lock the drill guide 30 in place. The stem portion 31 has an appropriate length to maintain the hollow shaft 35 at the distance X from the longitudinal axis AA of the first alignment arm 10. In this example the stem portion 31 extends under the slot 14B. Although the stem portion 31 extends under the slot 14B, the stem portion 31 is configured to maintain the hollow shaft 35 in the same plane P1 defined by the longitudinal axis AA and the first wire W1 extending through the through hole 16. (See FIG. 8). In the particular example shown in FIGS. 1B and 4B, the stem portion 31 has a jog 31A (labeled in FIG. 4B) that extends the stem portion 31 under the slot 14B.

In some embodiments of the surgical drill alignment guide assembly, the second alignment arm 20 has an alignment wire 25 provided therein and extends along the second alignment arm's longitudinal axis AAA. The alignment wire 25 is radio-opaque so that it is visible under fluoroscopy for checking the alignment of second alignment arm 20. Because the alignment wire 25 is positioned along the longitudinal axis AAA, the alignment wire 25 represents the longitudinal axis AAA under the fluoroscope.

In some embodiments, the drill guide 30 is attached to the second alignment arm 20. Regardless of whether the drill guide 30 is attached to the first alignment arm 10 or the second alignment arm 20, the drill guide 30 and the second alignment arm 20 are arranged so that the hollow shaft 35 is in the same plane as the longitudinal axis AAA of the second alignment arm 20, represented by the alignment wire 25 and in the same plane as the longitudinal axis AA of the first alignment arm 10, represented by the alignment wire 5.

As shown in FIGS. 1A and 1B, the first alignment arm 10 and the second alignment arm 20 are arranged so that the longitudinal axis AAA is placed at a distance X from a plane D2 that contains the longitudinal axis AA of the first alignment arm 10. The structure of the drill guide 30 is configured so that the hollow shaft 35 is also placed at the distance X from the plane D2 and the hollow shaft 35 is in a plane D1 that is orthogonal to the plane D2 and intersects the plane D2 along the longitudinal axis AA. This means that the longitudinal axis AAA of the second alignment arm 20 and the hollow shaft 35 are both lie in a plane D3 that is parallel to the plane D2 and orthogonal to the plane D1. Since the hollow shaft 35 has a cylindrical shape, when the present disclosure refers to the position of the hollow shaft 35, it is referring to the position of the longitudinal axis of the hollow shaft 35. This configuration among the first alignment arm 10, the second alignment arm 20, and the drill guide 30, enables a surgeon to use the surgical drill alignment guide assembly 100 to drill along the long axis A of a fifth metatarsal bone of a patient.

Figure 8:
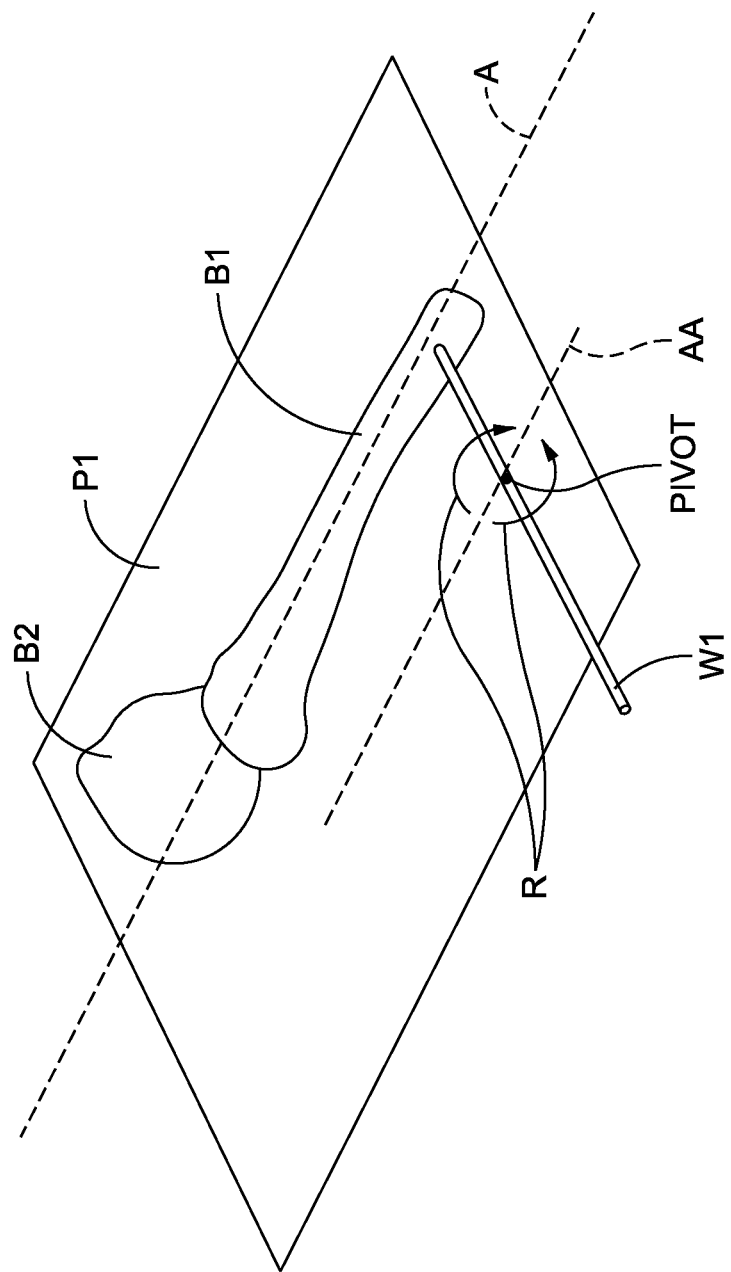
FIG. 8 is an illustration showing the spatial relationship among the fifth metatarsal bone B1, the first wire W1, the longitudinal axis AA of the first alignment arm 10, and the first alignment plane P1 defined by the first wire W1 and the long axis A of the fifth metatarsal bone B1, according to the present disclosure.
Figure 9:
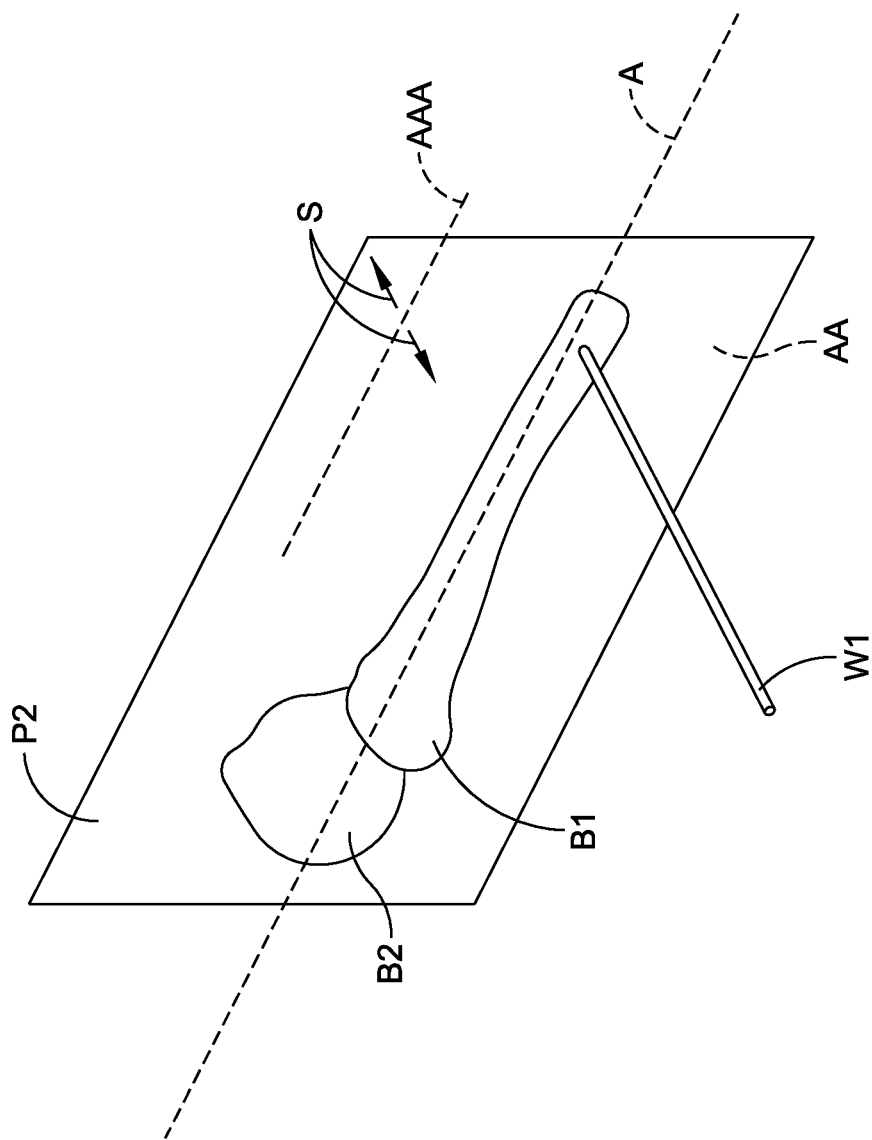
FIG. 9 is an illustration showing the spatial relationship among the fifth metatarsal bone B1, the long axis A of the fifth metatarsal bone B1, the longitudinal axis AAA of the second alignment arm 20, and the second alignment plane P2 according to the present disclosure.
Figure 10:
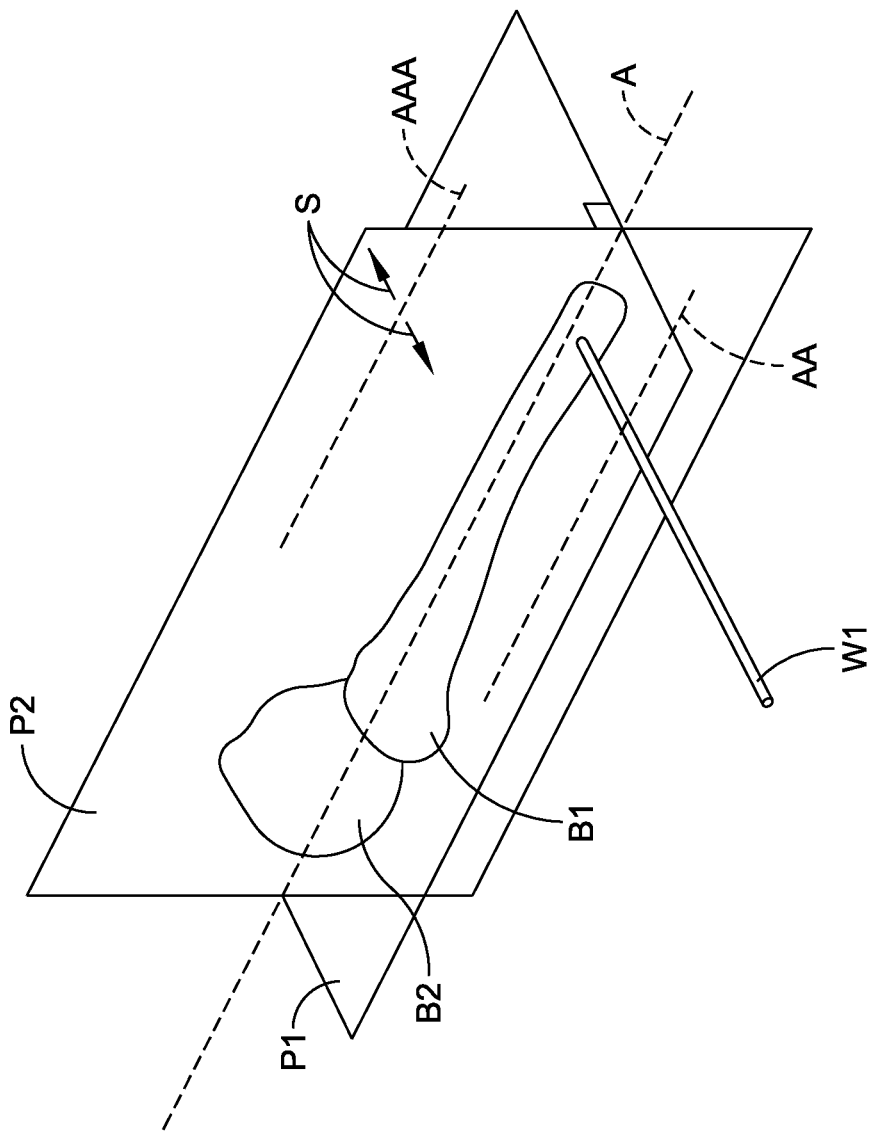
FIG. 10 is an illustration showing the components of FIGS. 8 and 9 and showing the orthogonal relationship between the first alignment plane P1 and the second alignment plane P2 according to the present disclosure.

Referring to FIGS. 8-10, in order to assist in describing the spatial alignment of the surgical drill alignment guide assembly 100 with the long axis A of a fifth metatarsal bone B1, we first define two alignment planes P1 and P2 that are orthogonal to each other. Referring to FIG. 8, the first alignment plane P1 is a plane that is defined by the long axis A of the fifth metatarsal bone B1 and the first wire W1 that is placed into the distal end of the fifth metatarsal bone B1 where the first wire W1 is substantially orthogonal to the long axis A of the fifth metatarsal bone B1. In other words, the long axis A and the first wire W1 lie in the first alignment plane P1. Referring to FIGS. 9 and 10, the second alignment plane P2 is orthogonal to the first plane P1 and intersects the first alignment plane P1 along the long axis A of the fifth metatarsal bone B1. In other words, the long axis A of the bone B1 lies in both planes P1 and P2.

Because the hollow shaft 35 is in the same first alignment plane P1 as the longitudinal axis AA of the first alignment arm 10, the hollow shaft 35 and the alignment wire 5 (of the first alignment arm 10) are in the same first plane P1. It should be noted that FIG. 10 does not show the alignment wire 5. However, the longitudinal axis AA of the first alignment arm 10 represents the location of the alignment wire 5 with respect to the first plane P1 because the alignment wire 5 is provided in the first alignment arm 10 along the first alignment arm's longitudinal axis AA, Some methods for using the drill alignment guide is also disclosed. In some embodiments, the method comprises the following steps. (a) The first wire W1 is inserted into a distal portion of a first bone B1 of a patient's foot or a hand with the first wire W1 oriented substantially orthogonal to the long axis A of the first bone B1. The point of entry for the first wire W1 is visually determined by the surgeon. The first wire W1 can either intersect and extends through the long axis A or extends along a trajectory that intersects the long axis A but does not go through the long axis A depending on the particular situation of the bone fracture or injury being attended to. The first wire W1 and the long axis A of the first bone B1 together defines the first alignment plane P1. The first alignment plane P1 is shown in FIG. 8. In other words, both the long axis A and the first wire W1 are in-plane in P1.

(b) Next, the first alignment arm 10 is slid over the first wire W1 through the first through hole 16 that is provided at the first end 11 of the first alignment arm 10. As described above in reference to FIG. 1A, the drill alignment guide assembly 100 is configured so that the first through hole 16 extends through the first alignment arm 10's longitudinal axis AA in a direction that is orthogonal to the longitudinal axis AA, the longitudinal axis AA reside in the plane D2. Therefore, once the first alignment arm 10 is slid over the first wire W1, the configuration of the drill alignment guide assembly 100 dictates that the planes D2 and D3 (shown in FIG. 1A) of the drill alignment guide assembly 100 are parallel to the second alignment plane P2 shown in FIG. 9.

(c) Next, an incision is made in the patient's foot or a hand near the proximal end of the first bone B1 and the drill guide 30 is moved into a position so that the tip 37 of the drill guide is contacting the proximal end of the first bone B1. For example, when used on a patient's foot for aligning to a fifth metatarsal bone, the drill guide 30 would be contacting the proximal end of the fifth metatarsal bone as appropriate. This example position is illustrated in FIGS. 6 and 7.

(d) Next, the surgeon aligns the second alignment arm 20 to the long axis A of the first bone B1 under fluoroscopy so that the second alignment arm's longitudinal axis AAA and the first bone B1's long axis A are in-plane in the second alignment plane P2. This aligning is accomplished by sliding the drill alignment guide assembly 100 along the first wire W1 in the directions illustrated with the arrows S in FIG. 10. The radio-opaque alignment wire 25 in the second alignment arm 20 is useful in this step because the alignment wire 25 representing the longitudinal axis AAA of the second alignment arm 20 is visible in fluoroscopy. Preferably, while viewing through a fluoroscope, the parallax cue 27 provided on the second alignment arm 20 is utilized to ensure that the surgeon is looking in-plane with the second alignment plane P2. In this method embodiment, because the drill guide 30 was placed in the proximity of the proximal end of the first bone B1, the second alignment arm 20 is already substantially close to the desired alignment position. Thus, only minor adjustments would be necessary to align the second alignment arm 20 to the long axis A of the first bone B1, (e) Once the second alignment arm 20 is in alignment with the long axis A, the surgeon inserts a second wire W2 through the at least one second through hole 18A of the first alignment arm and into a second bone B2 of the patient. This arrangement is shown in FIGS. 6 and 7. This secures the parallel alignment relationship between the longitudinal axis AA of the first alignment arm 10 and the long axis A of the first bone B1.

(f) Next, the surgeon visually aligns the longitudinal axis AA of the first alignment arm 10 with the long axis A of the first bone B1 in the first alignment plane P1 by adjusting the orientation of the first alignment arm 10 by pivoting the first alignment arm 10 about the first wire W1 in the directions R as shown in FIG. 8. In FIG. 8, the pivoting of the first alignment arm's longitudinal axis AA about the first wire W1 is illustrated by the directional arrows R.

(g) Then, the surgeon confirms the alignment between the first alignment arm 10 and the long axis A of the first bone B1 by fluoroscopy. This is accomplished by viewing through a fluoroscope along the first alignment plane P1 to ensure that the longitudinal axis AA of the first alignment arm 10 is parallel to the long axis A of the first bone B1 in the first alignment plane P1. Preferably, while viewing through a fluoroscope, the parallax cue 17 provided on the first alignment arm 10 is utilized to ensure that the surgeon is looking in-plane with the first alignment plane P1.

(h) If the longitudinal axis AA is not parallel to the long axis A, the step (f) is repeated until the first alignment arm 10 is aligned with the long axis A. When the parallel relationship between the longitudinal axis AA and the long axis A is achieved, the longitudinal axis AA and the long axis A are in-plane in the first alignment plane P1.

(i) At this point, the drill guide 30 is properly aligned to the long axis A of the first bone B1, i.e., aligned in both the first alignment plane P1 and the second alignment plane P2. Thus, a k-wire can be drilled through the hollow shaft 35 of the drill guide 30 and into the first bone B1 along its long axis A.

In some embodiments of the procedure, the first bone is a fifth metatarsal bone and the second bone is a mid-foot bone.

During this procedure, the surgeon has the option of locking the first alignment arm 10 to the first wire W1 sometime after the step (h) so that the arrangement of the first wire W1 and the first alignment arm 10 is secured. The surgeon has the option of locking the first alignment arm 10 to the second wire W2 sometime after the step (h) so that the arrangement of the second wire W2 and the first alignment arm 10 is secured. In other embodiments, the surgeon has the option of locking the first alignment arm 10 to the first wire W1 and the second wire W2 sometime after the step (h) so that the arrangement of the first wire W1, the second wire W2, and the first alignment arm 10 is secured.

As mentioned above, the configuration of the drill alignment guide 100 is such that it can be oriented so that the alignment procedure described above can be conducted with the second alignment arm 20 positioned on any side of the patient's body portion being operated on. For example, if the drill alignment guide assembly 100 is being used on a foot, the second alignment arm 20 can be positioned on the dorsal side of the patient's foot or on the plantar side of the patient's foot. Thus, at this point in the procedure, depending on whether the surgeon chose the dorsal side or the plantar side, the visual alignment of the second alignment arm 20 to the long axis A is conducted while viewing the second alignment arm 20 from the dorsal side or from the plantar side.

A method of using the drill alignment guide assembly 100 according to some other embodiments will now be described. The method comprises the following steps. (aa) The first wire W1 is inserted into a distal portion of a first bone B1 of a patient's foot or a hand with the first wire W1 oriented substantially orthogonal to the long axis A of the first bone B1. The point of entry for the first wire W1 is visually determined by the surgeon. The first wire W1 can either intersect and extends through the long axis A or extends along a trajectory that intersects the long axis A but does not go through the long axis A depending on the particular situation of the bone fracture or injury being attended to. The first wire W1 and the long axis A of the first bone B1 together defines the first alignment plane P1. The first alignment plane P1 is shown in FIG. 8. In other words, both the long axis A and the first wire W1 are in-plane in P1.

(bb) Next, the first alignment arm 10 is slid over the first wire W1 through the first through hole 16 that is provided at the first end 11 of the first alignment arm 10. As described above in reference to FIG. 1A, because the first through hole 16 extends through the first alignment arm 10's longitudinal axis AA in a direction that is orthogonal to the longitudinal axis AA, the configuration of the alignment guide assembly 100 dictates that the longitudinal axis AA reside in the plane D2 and that the plane D2 and the second alignment plane P2 (See FIG. 9) are now parallel to each other. while sharing the first wire W1 as the pivot.

(cc) Next, the surgeon visually aligns the first alignment arm 10 with the long axis A of the first bone B1 by pivoting the first alignment arm 10 about the first wire W1 in the directions shown by the arrows R shown in FIG. 8, until the first alignment arm's longitudinal axis AA and the first bone's long axis A are in-plane in the first alignment plane P1. In FIG. 8, the pivoting of the longitudinal axis AA about the first wire W1 is illustrated.

(dd) Then, the surgeon confirms the alignment between the first alignment arm 10 and the long axis A of the first bone B1 by fluoroscopy. This is accomplished by viewing through a fluoroscope along the first alignment plane P1 to ensure that the longitudinal axis AA of the first alignment arm 10 is parallel to the long axis A of the first bone B1. Preferably, while viewing through a fluoroscope, the parallax cue 17 provided on the first alignment arm 10 is utilized to ensure that the surgeon is looking in-plane with the first alignment plane P1.

(ee) If the longitudinal axis AA is not parallel to the long axis A, the steps (cc) and (dd) are repeated until the first alignment arm 10 is aligned with the long axis A. When the parallel relationship between the longitudinal axis AA and the long axis A is achieved, the longitudinal axis AA and the long axis A are in-plane in the first alignment plane P1.

(ff) Once the first alignment arm 10 is in alignment with the long axis A, the surgeon inserts a second wire W2 through the at least one second through hole 18A of the first alignment arm and into a second bone B2 of the patient. This arrangement is shown in FIGS. 6 and 7. This is to secure the parallel alignment relationship between the longitudinal axis AA of the first alignment arm 10 and the long axis A.

(gg) Next, the surgeon visually aligns the second alignment arm 20 to the long axis A of the first bone B1 by sliding the whole drill alignment guide assembly 100 along the lengths of the first and second wires W1 and W2 while looking down at the second alignment arm 20. This alignment step is for positioning the longitudinal axis AAA of the second alignment arm 20 in the second alignment plane P2. In FIG. 10, the sliding motion of the drill alignment guide assembly 100 is illustrated with the arrows S.

As mentioned above, the configuration of the drill alignment guide 100 is such that it can be oriented so that the alignment procedure described above can be conducted with the second alignment arm 20 positioned on any side of the patient's body portion being operated on. For example, if the drill alignment guide 100 is being used on a foot, the second alignment arm 20 can be positioned on the dorsal side of the patient's foot or on the plantar side of the patient's foot. Thus, at this point in the procedure, depending on whether the surgeon chose the dorsal side or the plantar side, the visual alignment of the second alignment arm 20 to the long axis A is conducted while viewing the second alignment arm 20 from the dorsal side or from the plantar side.

(hh) Next, the alignment between the second alignment arm 20 and the long axis A of the first bone B1 is verified using fluoroscopy. The radio-opaque alignment wire 25 in the second alignment arm 20 is useful in this step because the alignment wire 25 is visible in fluoroscopy. Preferably, while viewing through a fluoroscope, the parallax cue 27 provided on the second alignment arm 20 is utilized to ensure that the surgeon is looking in-plane with the second alignment plane P2.

(ii) If the alignment is not as desired and needs adjusting, the steps (gg) and (hh) are repeated until the second alignment arm 20 is aligned with the long axis A of the first bone B1.

(jj) Next, an incision is made in the patient's foot or a hand near the proximal end of the first bone B1 and the drill guide 30 is moved into a position so that the tip 37 of the drill guide is contacting the proximal end of the first bone B1. For example, when used on a patient's foot for aligning to a fifth metatarsal bone, the drill guide 30 would be contacting the proximal end of the fifth metatarsal bone as appropriate. This example position is illustrated in FIGS. 6 and 7. Because the hollow shaft 35 of the drill guide 30 is in-plane with the longitudinal axis AA in the plane D1 and in-plane with the longitudinal axis AAA, the hollow shaft 35 will be in axial alignment with the long axis A of the first bone B1.

During this procedure, the surgeon has the option of locking the first alignment arm 10 to the first wire W1 sometime after the step (ii) so that the arrangement of the first wire W1 and the first alignment arm 10 is secured. The surgeon has the option of locking the first alignment arm 10 to the second wire W2 sometime after the step (ii) so that the arrangement of the second wire W2 and the first alignment arm 10 is secured. In other embodiments, the surgeon has the option of locking the first alignment arm 10 to the first wire W1 and the second wire W2 sometime after the step (ii) so that the arrangement of the first wire W1, the second wire W2, and the first alignment arm 10 is secured.

At this point, the long axis A, the longitudinal axis AA, and the longitudinal axis AAA are in the desired alignment relative to each other. This alignment is illustrated in FIG. 10 where the longitudinal axis AA and the long axis A are in-plane in the first alignment plane P1 and the longitudinal axis AAA and the long axis A are in-plane in the second alignment plane P2.

The method can further comprise a step of locking the drill guide 30 in place. In the examples illustrated here, the drill guide 30 can be locked in place by tightening the locking nut 43. After the drill guide 30 is locked in place a k-wire is inserted or thrown through the hollow shaft 35 of the drill guide 30 and into the first bone B1 following the trajectory set by the drill guide 30. Then, a drill bit is inserted through the hollow shaft 35 over the k-wire for drilling into the first bone.

In some embodiments, the first bone B1 is a fifth metatarsal bone of a patient and the second bone B2 is a mid-foot bone associated with the fifth metatarsal bone. In some embodiments, the first bone B1 is a first metatarsal bone of a patient and the second bone B2 is a mid-foot bone associated with the first metatarsal bone.

According to some other embodiments of the method, the second alignment arm 20 can be aligned with the long axis A of the first bone B1 first. Then, the first alignment arm 10 can be aligned with the long axis A of the first bone B1 before the second wire W2 is secured to the second bone B2. Accordingly, this alternate method comprises: (aaa) inserting the first wire into a first bone of a patient (the first wire can be inserted either into the distal portion or into the proximal portion of the first bone) wherein the first wire is substantially orthogonal to the first bone's long axis; (bbb) sliding the first alignment arm over the first wire through the first through hole; (ccc) aligning the second alignment arm to the long axis of the first bone so that the second alignment arm's longitudinal axis and the first bone's long axis are in-plane in the second alignment plane; (ddd) confirming the alignment between the second alignment arm and the long axis of the first bone by fluoroscopy; (eee) repeating (ccc) and (ddd) if necessary, until the second alignment arm is aligned with the long axis of the first bone; (fff) aligning the first alignment arm to the long axis of the first bone so that the first alignment arm's longitudinal axis and the first bone's long axis are in-plane in the first alignment plane; (ggg) confirming the alignment between the first alignment arm and the long axis of the first bone by fluoroscopy; (hhh) repeating (fff) and (ggg) if necessary, until the first alignment arm is aligned with the long axis; (iii) inserting the second wire through the at least one second through hole of the first alignment arm and into a second bone of the patient; (jjj) locking the first alignment arm to the first wire so that the arrangement of the first wire and the first alignment arm is fixed; (kkk) locking the first alignment arm to the second wire so that the arrangement of the second wire and the first alignment arm is fixed; and (lll) moving the drill guide into place so that the hollow shaft of the drill guide is alignment with the long axis of the first bone. In some embodiments of this procedure, the steps (jjj) and (kkk) can be optional and the surgeon can opt to perform the steps (jjj) and (kkk) individually sometime after the step (iii) or perform the steps (jjj) and (kkk) together sometime after step (iii). In steps (ddd) and (ggg) in this embodiment, while viewing through a fluoroscope, the parallax cue 17 provided on the first alignment arm 10 and the parallax cue 27 provided on the second alignment arm 20 are utilized to ensure that the surgeon is looking in-plane with the associated first alignment plane P1 and the second alignment plane P2.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A guide assembly comprising:
   a first arm having a first end, a second end, and an axis extending from the first end to the second end, the first end of the first arm defining a first hole and at least one second hole provided between the first hole and the second end,
   the first hole extending through the first end of the first arm at an angle to and intersecting with the axis of the first arm and the at least one second hole extending through the first arm at an angle to the axis of the first arm;

a second arm having a first end, a second end, and an axis extending between the first end and the second end, the first end of the second arm being attached to the first end of the first arm, wherein the second arm is oriented so that its axis is in parallel relation to the axis of the first arm; and a guide attached to the first arm or the second arm, the guide comprising an arm having a hollow shaft for receiving a drill bit or a k-wire, wherein the hollow shaft extends in parallel relation to the axis of the first arm and the axis of the second arm, such that the hollow shaft is in-plane with the first arm's axis in a first plane, and in-plane with the second arm's axis in a second plane so that the first plane and the second plane are at an angle to each other.

2. The guide assembly of claim 1, wherein the guide is slidably attached to the second end of the first arm, wherein the guide is slidable along the axis of the first arm.

3. The guide assembly of claim 1, wherein the guide is slidably attached to the second end of the second arm, wherein the guide is slidable along the axis of the second arm.

4. The guide assembly of claim 1, wherein the second arm has an alignment wire provided along the second arm's axis and the alignment wire is in the second plane.

5. The guide assembly of claim 4, wherein the alignment wire in the second arm is radio-opaque.

6. The guide assembly of claim 1, wherein the first arm has an alignment wire provided along the axis of the first arm and the alignment wire is located in the first plane and the second plane.

7. The guide assembly of claim 6, wherein the alignment wire in the first arm is radio-opaque.

8. The guide assembly of claim 1, wherein the first hole and the at least one second hole extend through the first arm at an angled orientation to the axis of the first arm.

9. The guide assembly of claim 8, wherein the first hole is configured to maintain the location of the first wire within the first hole and the at least one second hole is configured to maintain the position of the second wire that is received in the at least one second hole.

10. The guide assembly of claim 1, wherein the first arm and the second arm are provided with parallax cues for use when checking the alignment of the guide assembly through a fluoroscope.

11. A surgical method for using a guide assembly comprising:

(a) providing a guide assembly including a first arm having a first end, a second end, and an axis extending from the first end to the second end, the first end of the first arm defining a first hole and at least one second hole provided between the first hole and the second end, were the first hole extends through the first end of the first arm at an angle to and intersecting the axis of the first arm and the at least one second hole extending through the first arm at an angle to the axis of the first arm; a second arm having a first end, a second end, and an axis extending between the first end and the second end, the first end of the second arm being attached to the first end of the first arm, with the second arm being oriented so that its axis is in parallel relation to the axis of the first arm; and a guide attached to the first arm or the second arm, the guide includes an arm having a hollow shaft for receiving a drill bit or a k-wire, the hollow shaft extending in parallel relation to the axis of the first arm and the axis of the second arm, such that the hollow shaft is in-plane with the first arm's axis in a first plane, and in-plane with the second arm's axis in a second plane so that the first plane and the second plane are at an angle to each other;

(b) inserting the first wire into a distal portion of a first bone of a patient wherein the first wire is oriented substantially orthogonal to the first bone's long axis, whereby the first wire and the long axis of the first bone define a first alignment plane;

(c) sliding the first arm over the first wire through the first hole;

(d) making an incision near the proximal end of the first bone and positioning the guide so that the tip of the guide is contacting the proximal end of the first bone;

(e) aligning the second arm to the long axis of the first bone under fluoroscopy so that the second arm's axis and the first bone's long axis are in-plane in a second alignment plane that is orthogonal to the first alignment plane;

(f) inserting a second wire through the at least one second hole of the first arm and into a second bone of the patient thus securing the parallel alignment relationship between the axis of the first arm and the long axis of the first bone;

(g) visually aligning the axis of the first arm with the long axis of the first bone in the first alignment plane by adjusting the orientation of the first arm by pivoting the first arm about a first wire;

(h) confirming the alignment between the axis of the first arm and the long axis of the first bone by fluoroscopy; and (i) repeating the step (g) if the axis of the first arm is not aligned with the long axis of the first bone.

12. The surgical method of claim 11, further comprising a step (j) of drilling a k-wire through the hollow shaft of the guide and into the first bone.

13. The surgical method of claim 11, further comprising a step of maintaining the first arm to the first wire sometime after the step (h) so that the arrangement of the first wire and the first arm is fixed.

14. The surgical method of claim 11, wherein the first bone is a fifth metatarsal bone and the second bone is a mid-foot bone.

15. The surgical method of claim 11, further comprising the step of maintaining the guide in place after the step (i).

16. The surgical method of claim 11, wherein in step (e), a parallax cue provided on the second arm is utilized to ensure that the fluoroscopy is being taken in-plane with the second alignment plane.

17. The surgical method of claim 11, wherein in step (h), a parallax cue provided on the first arm is utilized to ensure that the fluoroscopy is being taken in-plane with the first alignment plane.

* * * * *